(12) United States Patent
Khandaker et al.

(10) Patent No.: US 10,286,103 B2
(45) Date of Patent: *May 14, 2019

(54) METHOD AND APPARATUS TO CONTROL THE HETEROGENEOUS FLOW OF BONE CEMENT AND IMPROVE OSSEOINTEGRATION OF CEMENTED IMPLANT

(71) Applicant: University of Central Oklahoma, Edmond, OK (US)

(72) Inventors: Morshed Khandaker, Edmond, OK (US); Shahram Riahinezhad, Fort Lee, NJ (US)

(73) Assignee: University of Central Oklahoma, Edmond, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/976,615

(22) Filed: May 10, 2018

(65) Prior Publication Data
US 2018/0256778 A1 Sep. 13, 2018

Related U.S. Application Data

(63) Continuation of application No. 15/674,309, filed on Aug. 10, 2017, now Pat. No. 9,974,883.
(Continued)

(51) Int. Cl.
*A61F 2/30* (2006.01)
*A61L 24/10* (2006.01)
(Continued)

(52) U.S. Cl.
CPC .......... *A61L 24/102* (2013.01); *A61F 2/2846* (2013.01); *A61F 2/30907* (2013.01);
(Continued)

(58) Field of Classification Search
CPC ............... A61F 2/2846; A61F 2/30723; A61F 2/30734; A61F 2/30907; A61F 2002/30736; A61F 2002/30919
See application file for complete search history.

(56) References Cited

U.S. PATENT DOCUMENTS

| | | | |
|---|---|---|---|
| 9,359,694 B2 | 6/2016 | Khandaker et al. | |
| 2011/0066242 A1 | 3/2011 | Lu et al. | |
| 2016/0374820 A1 | 12/2016 | Khandaker et al. | |

FOREIGN PATENT DOCUMENTS

| | | |
|---|---|---|
| CN | 103893828 A | 7/2014 |
| CN | 104906637 A | 9/2015 |

OTHER PUBLICATIONS

Wenying Liu, Electrospun Nanofibers for Regenerative Medicine, 2012, Adv Healthc Mater, pp. 1-28.*
(Continued)

*Primary Examiner* — Brian A Dukert
(74) *Attorney, Agent, or Firm* — Berenato & White, LLC

(57) ABSTRACT

The present invention provides processes for combined applications of making grooves on an implant surface, applying MgO nanoparticles with PMMA cement, restricting the cement movement by PCL nanofiber and tethering biomolecules with PCL nanofiber to enhance mechanical stability and osseointegration of PMMA cement with bone. This is achieved through enhanced osteoconductive properties, roughness, and less viable fracture originating sites at the bone-cement interface. Such combined applications of nanoparticle and nanofiber on the mechanical stability and osseointegration of cemented implant is heretofore unknown, but as provided by the present invention can solve the debonding problem of cemented implant from bone.

13 Claims, 16 Drawing Sheets

Related U.S. Application Data

(60) Provisional application No. 62/373,786, filed on Aug. 11, 2016.

(51) Int. Cl.
| | |
|---|---|
| *A61F 2/28* | (2006.01) |
| *A61K 38/18* | (2006.01) |
| *A61L 24/00* | (2006.01) |
| *A61L 24/02* | (2006.01) |
| *A61L 24/06* | (2006.01) |
| *A61B 17/86* | (2006.01) |
| *A61B 17/56* | (2006.01) |
| *A61F 2/36* | (2006.01) |

(52) U.S. Cl.
CPC ...... *A61K 38/1841* (2013.01); *A61K 38/1875* (2013.01); *A61L 24/0015* (2013.01); *A61L 24/0089* (2013.01); *A61L 24/0094* (2013.01); *A61L 24/02* (2013.01); *A61L 24/06* (2013.01); *A61L 24/108* (2013.01); *A61B 17/866* (2013.01); *A61B 2017/564* (2013.01); *A61B 2017/8655* (2013.01); *A61F 2/30723* (2013.01); *A61F 2/30734* (2013.01); *A61F 2/3601* (2013.01); *A61F 2002/30736* (2013.01); *A61F 2002/30919* (2013.01); *A61F 2310/00011* (2013.01); *A61L 2300/102* (2013.01); *A61L 2300/252* (2013.01); *A61L 2300/404* (2013.01); *A61L 2300/414* (2013.01); *A61L 2400/12* (2013.01); *A61L 2430/02* (2013.01)

(56) References Cited

OTHER PUBLICATIONS

Khandaker, M.; Vaughan, M.; Coles, A.; Jamadagni, H.; Wolf, R.; Williams, W. Application of polycaprolactone nanofibers and mgo nanoparticles for a cemented implant surgery. In Proceedings of the 2017 Orthopaedic Research Society (ORS) Annual Meeting, San Diego, CA, USA, Mar. 19-22, 2017.

Po-Yee Lui, P.; Zhang, P.; Chan, K.-M.; Qin, L. Biology and augmentation of tendon-bone insertion repair. J. Orthop. Res. Surg. Res. 2010, 5.

Apedo, K.L.; Munzer, C.; He, H.; Montgomery, P.; Serres, N.; Fond, C.; Feugeas, F. Cement paste surface roughness analysis using coherence scanning interferometry and confocal microscopy. Mater. Charact. 2015, 100, 108-119.

Sultanova, Z.; Kaleli, G.; Kabay, G.; Mutlu, M. Controlled release of a hydrophilic drug from coaxially electrospun polycaprolactone nanofibers. Int. J. Pharm. 2016, 505, 133-138.

Wang, H.B.; Mullins, M.E.; Gregg, J.M.; Hurtado, A.; Oudega, M.; Trombley, M.T.; Gilbert, R.J. Creation of highly aligned electrospun poly-l-lactic acid fibers for nerve regeneration applications. J. Neural Eng. 2009, 6, 016001.

Deravi, L.F.; Sinatra, N.R.; Chantre, C.O.; Nesmith, A.P.; Yuan, H.; Deravi, S.K.; Goss, J.A.; MacQueen, L.A.; Badrossamy, M.R.; Gonzalez, G.M.; et al. Design and fabrication of fibrous nanomaterials using pull spinning. Macromol. Mater. Eng. 2017, 302.

Khandaker, M.; Vaughan, M.; Morris, T.; White, J.; Meng, Z. Effect of additives particles on mechanical, thermal and cell functions properties of poly (methyl methacrylate) cement. Int. J. Nanomed. 2014, 9, 2699-2712.

Graham, J.; Ries, M.; Pruitt, L. Effect of bone porosity on the mechanical integrity of the bone-cement interface. J. Bone Jt. Surg. Am. vol. 2003, 85A, 1901-1908.

Kwon, I.K.; Kidoaki, S.; Matsuda, T. Electrospun nano—to microfiber fabrics made of biodegradable copolyesters: Structural characteristics, mechanical properties and cell adhesion potential. Biomaterials 2005, 26, 3929-3939.

Kumbar, S.G.; James, R.; Nukavarapu, S.P.; Laurencin, C.T. Electrospun nanofiber scaffolds: Engineering soft tissues. Biomed. Mater. 2008, 3.

Kim, G.H. Electrospun pcl nanofibers with anisotropic mechanical properties as a biomedical scaffold. Biomed. Mater. 2008, 3.

Chong, L.H.; Hassan, M.I.; Sultana, N. Electrospun polycaprolactone (pcl) and pcl/nano-hydroxyapatite (pcl/nha)-based nanofibers for bone tissue engineering application. In Proceedings of the 10th Asian Control Conference (ASCC), Kota Kinabalu, Malaysia, 31 Mal Jun. 3, 2015; pp. 1-4.

Moursi, A.M.; Winnard, A.V.; Winnard, P.L.; Lannutti, J.J.; Seghi, R.R. Enhanced osteoblast response to a polymethylmethacrylate-hydroxyapatite composite. Biomaterials 2002, 23, 133-144.

Mahalingam, S.; Edirisinghe, M. Forming of polymer nanofibers by a pressurised gyration process. Macromol. Rapid Commun. 2013, 34, 1134-1139.

Saha, S.; Pal, S. Improvement of mechanical properties of acrylic bone cement by fiber reinforcement. J. Biomech. 1984, 17, 467-478.

Kanungo, I.; Fathima, N.N.; Rao, J.R.; Nair, B.U. Influence of pcl on the material properties of collagen based biocomposites and in vitro evaluation of drug release. Mater. Sci. Eng. C Mater. Biol. Appl. 2013, 33, 4651-4659.

Ries, M.D.; Rauscher, L.A.; Hoskins, S.; Lott, D.; Richman, J.A.; Lynch, F. Intramedullary pressure and pulmonary function during total knee arthroplasty. Clin. Orthop. Relat. Res. 1998, 356, 154-160.

Invitrogen. Click-it® Edu Imaging Kits. Available online: https://tools.thermofisher.com/content/sfs/manuals/mp10338.pdf (accessed on Oct. 26, 2017).

Zupancic, S.; Baumgartner, S.; Lavric, Z.; Petelin, M.; Kristl, J. Local delivery of resveratrol using polycaprolactone nanofibers for treatment of periodontal disease. J. Drug Deliv. Sci.Technol. 2015, 30 Pt B, 408-416.

Wu, X.; Mahalingam, S.; VanOosten, S.K.; Wisdom, C.; Tamerler, C.; Edirisinghe, M. New generation of tunable bioactive shape memory mats integrated with genetically engineered proteins. Macromol. Biosci. 2017, 17.

Moffat, K.L.; Wang, I.N.; Rodeo, S.A.; Lu, H.H. Orthopedic interface tissue engineering for the biological fixation of soft tissue grafts. Clin. Sports Med. 2009, 28, 157-176.

Travan, A.; Marsich, E.; Donati, I.; Foulc, M.-P.; Moritz, N.; Aro, H.T.; Paoletti, S. Polysaccharide-coated thermosets for orthopedic applications: From material characterization to in vivo tests. Biomacromolecules 2012, 13, 1564-1572.

Lim, J.Y.; Shaughnessy, M.C.; Zhou, Z.; Noh, H.; Vogler, E.A.; Donahue, H.J. Surface energy effects on osteoblast spatial growth and mineralization. Biomaterials 2008, 29, 1776-1784.

Im, B.J.; Lee, S.W.; Oh, N.; Lee, M.H.; Kang, J.H.; Leesungbok, R.; Lee, S.C.; Ahn, S.J.; Park, J.S. Texture direction of combined microgrooves and submicroscale topographies of titanium substrata influence adhesion, proliferation, and differentiation in human primary cells. Arch. Oral Biol. 2012, 57, 898-905.

Ferraz, E.P.; Sa, J.C.; De Oliveira, P.T.; Alves, C., Jr.; Beloti, M.M.; Rosa, A.L. The effect of plasma-nitrided titanium surfaces on osteoblastic cell adhesion, proliferation, and differentiation. J. Biomed. Mater. Res. Part A 2014, 102, 991-998.

Zankovych, S.; Diefenbeck, M.; Bossert, J.; Mückley, T.; Schrader, C.; Schmidt, J.; Schubert, H.; Bischoff, S.; Faucon, M.; Finger, U.; et al. The effect of polyelectrolyte multilayer coated titanium alloy surfaces on implant anchorage in rats. Acta Biomater. 2013, 9, 4926-4934.

Biggs, M.; Dalby, M.; Wilkinson, C.; Gadegaard, N.; Richards, G. The influence of nanoscale biomimetic structures on osteoblast adhesion. Comp. Biochem. Physiol. Part A Mol. Integr. Physiol. 2007, 146, S64.

Wagner, H.D.; Cohn, D. Use of high-performance polyethylene fibres as a reinforcing phase in poly(methylmethacrylate) bone cement. Biomaterials 1989, 10, 139-141.

\* cited by examiner

METHOD AND APPARATUS TO CONTROL THE HETEROGENEOUS FLOW OF BONE CEMENT AND IMPROVE OSSEOINTEGRATION OF CEMENTED IMPLANT

CROSS REFERENCES TO RELATED APPLICATIONS

This application claims benefit of U.S. patent application Ser. No. 15/674,309, filed Aug. 10, 2017 by the University of Central Oklahoma (Applicant,) entitled "Method and apparatus to control the heterogeneous flow of bone cement and improve osseonintegration of cemented implant" the entire disclosure of which is incorporated herein by reference in its entirety for all purposes. This application claims the benefit of U.S. Provisional Patent Application No. 62/373,786 filed on Aug. 11, 2016 in the name of Morshed Khandaker and Shahram Riahinezhad, which is expressly incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with government support under 8P20GM103447 awarded by the United States National Institutes of Health. The government has certain rights in the invention.

FIELD OF THE INVENTION

The present invention generally relates to the field of prosthetics. More specifically, the invention relates to attachment of orthopedic implants to bone using orthopedic bone cement. Cemented fixation of titanium (Ti) with bone are commonly used in orthopedic surgeries. Cemented fixation, mainly used for osteoporotic bone, requires bone cement to hold the Ti based prostheses in place. Since implant loosening usually occurs in cemented joint replacement surgeries from lack of osseointegration of implant (Ti or bone cement) with bone, clinically better osseointegration of implant with bone is required to prevent or at least diminish loosening over time to preclude repeat surgeries. The present invention solves the loosening problem of cemented implant surgeries both orthopedic and orthodontic applications.

BACKGROUND OF THE INVENTION

Cemented fixation of an implant, mainly used for osteoporotic bone, requires bone cement to hold the implant in place. Although considerable advances have already been made to improve the biological performance of cement, the ideal long-term mechanical stability of a cemented implant is still not achieved. An ideal cementing material for cemented surgeries should have surface energy and mechanical interlock to ensure a long-lasting fixation between implant-cement and cement-bone interfaces. The critical task for creating a long lasting tissue-implant interface resides in achieving the functional integration to mimic native tissue-tissue failure response. Appropriate mechanical interlock and adequate osseointegration is present between the joining tissues at natural tissue-tissue interfaces. Since bone cement is a bio-inert material, in case of natural tissue-cement interface in cemented joint, the joining of cement with bone is done by mechanical interlock. The goal of this innovation is to increase the osseointegration at the tissue-cement interface by improving the bioactivity of cement so that it will mimic native tissue-tissue failure response under functional loading.

The debonding of the PolyMethylMethAcrylate (PMMA) cement from bone in cemented joint replacement is frequently reported in literature. In the case of total cemented joint replacements, implant loosening occurs due to debonding of the bone-cement interface due to poor osseointegration of bone cement with bone or weakening of bone due to local high stressed area. Heterogeneous flow of bone cement around the implants due to the porosity of trabecular bone has been observed. Localized fractures may occur at the narrow confined tissue-cement interface by a relatively smaller force in compare to failure force of bone due to this heterogeneous flow of cement (FIG. 1). PMMA is a bio-inert material. Current trend of biomaterial research is focused on the addition of bio-additives with cement to solve the debonding problem by improving the osseointegration of cements with bone. The purpose of this innovation is to coat PMMA at the bone/cement interface by nanofiber immobilized with drugs to improve the biocompatibility PMMA cement without the diminishing the mechanical properties of PMMA at in vivo condition.

Nanofibers are a simple, scalable, inexpensive and supplementary surface treatment technique for biomaterials that have been implemented by various researchers. Most of research of the nanofiber applications on cement is focused on improving the mechanical properties of cement rather than improving the bioactivity of bone cement. For example, Wagner and Cohn used high performance polyethylene fibers as a reinforcing phase in PMMA bone cement. The authors found that the surface coating treatments of the Spectra 900 polyethylene fibers apparently did not significantly affect the mechanical properties of the PMMA bone cement. Saha and Pal found that addition of 1-2% by weight of graphite and up to 6% aramid fibers into PMMA cement reinforced significantly the mechanical strength of PMMA. However, the previous authors did not conduct cell viability studies to evaluate the effect of their fiber treatments on the biocompatibility of PMMA. Nanofibers can be biomineralised by immobilization of functional proteins and minerals with the fiber. Wu. et al. produced aligned poly(l-lactide)/poly(methyl methacrylate) binary blend fibers and mats loaded with a chimeric green fluorescence protein having a bioactive peptide with hydroxyapatite binding and mineralization property by pressurized gyration. The previous authors' research showed that nanofiber can have controllable inherent mineralization abilities through integrated bioactivity. However, no method has been proposed by which to apply nanofiber membrane on cement to improve its biomechanical properties. In our research, we showed a technique to put the electrospun fiber membrane on the surface of set PMMA cement. Our recent research manuscript in Nanomaterial Journal titled "Use of Polycaprolactone Electrospun Nanofibers as a Coating for Poly (methylmethacrylate) Bone Cement" showed how to apply fiber membrane on cement for biomechanical characterization (FIG. 2). But the problem is how a clinician is going to apply such fiber membrane in real life for cemented surgeries. The rationale for using bone cement is that it is injected in the dough phase of mechanical properties during the polymerisation process. It is used as "grout" so a space filler to give either an interference fit between the implant and the supporting bone or to fill defects such as when it is used for cemented joint surgeries. In our innovation, we have developed and described a process by which the nanofiber membrane of any specific size or shape, with or without drugs can be placed on the surface of set cement. Our invented technique can also control the flow of cement into bone cavities using the flexibility and strength of electrospun nanofiber membrane.

SUMMARY OF THE INVENTION

Electrospinning is a process by which fibers with micron- to nanometer diameters can be deposited on a substrate from an electrostatically driven jet of polymer solution through a needle. These fibers have a high surface area-to-volume ratio, which can be used to produce an electrospun nanofiber (ENF) membrane for biomedical applications. Polycaprolactone (PCL) nanofibers can be produced using an electrospinning process that is biocompatible and nontoxic. An electrospun nanofiber membrane (ENFM) has been developed in our innovation that can not only improve the osseointegration of cement with adjoining tissue, but also can control the flow of cement into trabecular bone cavities. We have demonstrated the improvement of biomechanical performance of poly methyl methacrylate (PMMA) cement and tissue-cement interface resulting from the addition of antibacterial and osteoconductive nanoparticles (e.g. MgO, silver, $TiO_2$, ZnO) with PMMA. Our in vitro studies using bone cells and in vivo using rabbit model shows that the ENFM coating increased the biocompatibility of cement that lead to better mechanical stability and osseointegration of cement with tissue. Further improvement of biomechanical performance of poly methyl methacrylate (PMMA) cement and tissue-cement interface was achieved with the addition of antibacterial and osteoconductive nanoparticles (e.g. MgO, silver, TiO2, ZnO) with PCL ENFM.

Combined applications of making groove or ion deposition on implant surface (co-pending application Ser. No. 15/467,652 by the present inventor), applying nanoparticles additives with PMMA cement, immobilization of osteoconductive nanomaterials with ENF and construction of nanofiber membrane with adequate stiffness to control the cement movement in to the bone has be found to enhance mechanical stability and osseointegration of PMMA cement with bone. Our research has demonstrated this method through clinical application of the use of nanofiber membrane for cemented implant surgeries in an animal model. Such combined applications of nanoparticle and nanofiber on the mechanical stability and osseointegration of cemented implant is heretofore unknown, but as provided by the methods of the present invention can solve the debonding problem of cemented implant from bone.

One objective of the present invention is to use grooving on Ti produced by the nanofabrication technique (disclosed in co-pending application Ser. No. 15/467,652 by the present inventor and incorporated herein by reference), nanoparticles additives with bone cement, and bone growth protein/ minerals with PCL nanofiber membrane to improve the osseointegration of cemented implant from bone.

In one major aspect, microgrooves are fabricated on an implant by controlled formation of titanium nitride (TiN) ridges and the microgrooves are anchored in bone by nanoparticles additives (NPA) (e.g. MgO, Hydroxyapatite, chitosan, etc.) incorporated with bone cement to produce higher biomechanical advantages compared to non-grooved Ti implants and non-NPA cemented implants due to increased biological compatibility of treated Ti and cement.

In another aspect, microgrooves are coupled with poly- ε-caprolactone nanofiber membrane (PCL NFM) to improve the biomechanical performances of Ti to advance in-vivo tissue-to-implant osseointegration and produce faster healing times.

In another aspect, microgrooves are coupled with growth factors (e.g. collagen) immobilized-poly-ε-caprolactone nanofiber membrane (CG-PCL NFM) and nanoparticles additives (NPA) poly-ε-caprolactone nanofiber membrane (NPA-PCL NFM) coating are coupled with the biomechanical functions of Ti implant to produce higher biomedical advantages compared to PCL NFM due to the increased osteoinductive and antimicrobial nature of the coatings.

In another aspect, ENF membrane can be used to act as resource for cell adhesion matrix protein (e.g. fibronectin, cellulous) to the adjoining bone tissue to produce better osseointegration with the cement surface.

In another aspect, prolonged antimicrobial and osteoinductive activities of PCL NFM is made possible by tethering the antimicrobial and osteoinductive molecules with PCL fiber (MgO, ZnO, Ag) in the ENF.

In another aspect, further improvement of cement-bone interface using PCL ENF cup is made possible by immobilization of bone growth protein and molecules (rhBMP, TGF-β) with the PCL ENF.

DETAIL DESCRIPTION

The present invention provides a novel cementing technique to solve the debonding problem and improve the mechanical stability and osseointegration of cemented implant with bone. Implants can be coated with a functional coating to increase the osteoinductive properties, and thereby to improve osseointegration of an implant. Methods (incorporated herein by reference in their entireties) disclosed by the present inventor in U.S. Pat. No. 9,359,694 and co-pending U.S. application Ser. Nos. 15/439,650 and 15/467,652 provide a set of steps (e.g. grooving, plasma oxidizing) by which a nanofiber membrane, composed of Collagen glycosaminoglycan (CG) and Polycaprolecton (PCL) electrospun nanofiber (ENF) can be coated on Ti, a widely-used orthopedic and orthodontic implant material. Both in vitro and in vivo evidence indicated that machine sawing of microgrooves on titanium (Ti) implants and coating the microgrooves with collagen-poly-ε-caprolactone nanofiber matrix (CG-PCL NFM) significantly improves mechanical stability and osseointegration of Ti (M Khandaker, S. Riahinezhad, W. Williams, R. Wolf, "Microgroove and Collagen-poly(e-caprolactone) Nanofiber Mesh Coating Improves the Mechanical Stability and Osseointegration of Titanium Implants." Nanomaterials 2017, 7 (6), 145; doi: 10.3390/nano7060145). A significantly improved osseointegration of CG-PCL NFM coated Ti over non-coated Ti was observed during the development of the disclosed methods (Khandaker M, Riahinezhad S, Li Y, Sultana F, Morris T, Vaughan M, Wolf R, Williams W. "Effect of collagen-polycaprolactone extracellular matrix on the in vitro cytocompatibility and in vivo bone responses of titanium." Journal of Medical and Biological Engineering, 38, 1-14, DOI 10.1007/s40846-017-0312-7, NIHMSID 895164).

Figure 1:
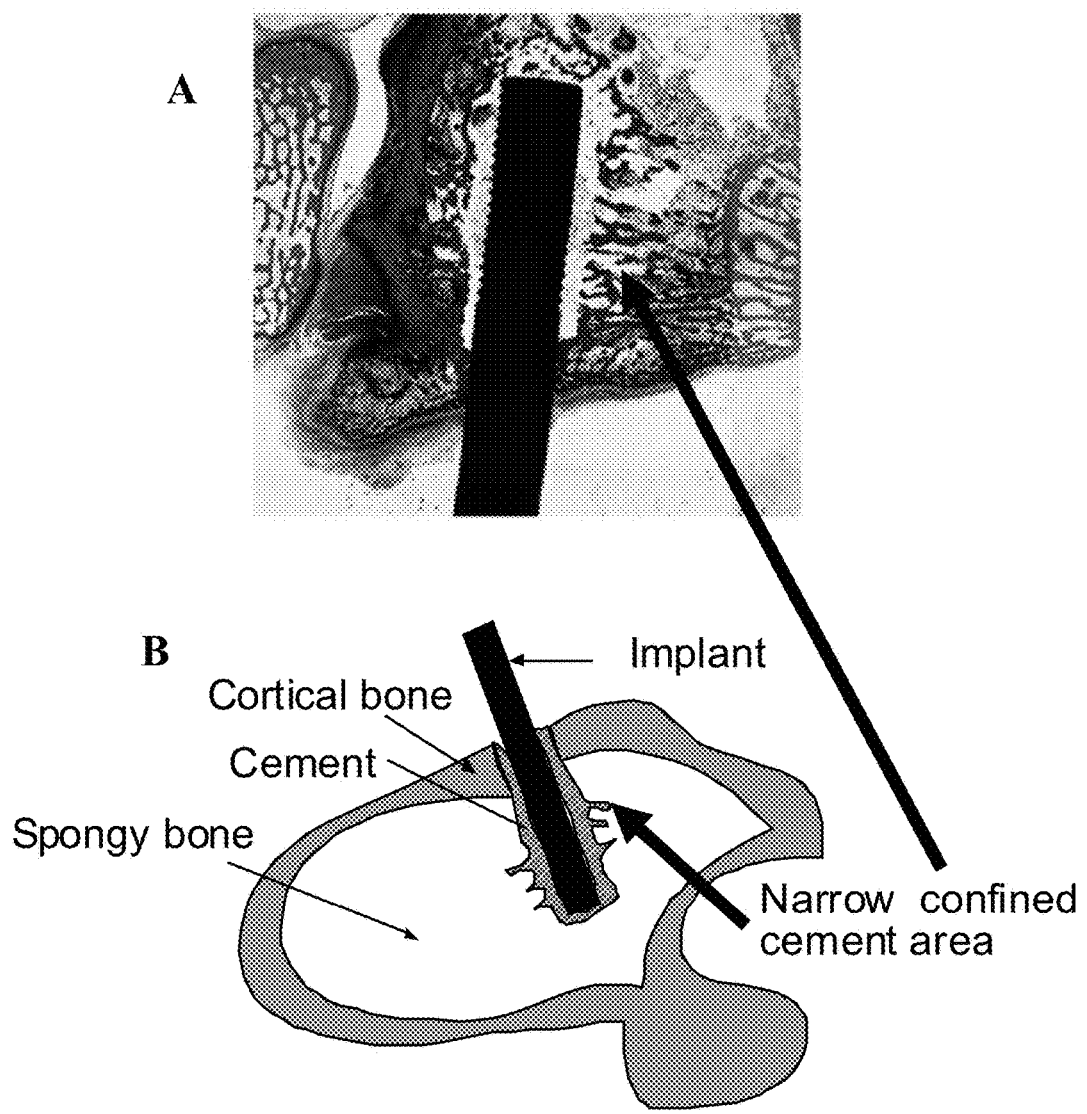
FIG. 1 is a non-limiting diagram showing the heterogeneous flow of bone cement around the implants for a cemented implant surgery resulting from the porosity of bone: (A) histology image of a cemented implant and (B) a corresponding schematic representation. In the images the bold arrows show the existence of narrowly confined cement areas in the spongy bone.

Referring to FIG. 1, image A and corresponding diagram B shows a clinical problem where heterogeneous flow of bone cement around the implant to the adjacent bone tissue has been observed due to the porosity of bone. Since significantly more cracks are associated with the interdigitated area and the cement/bone interface than with the implant/cement interface, there is a high probability that localized fractures may occur at the narrowly confined cement/bone interfaces shown in corresponding diagram B in FIG. 1 due to this heterogeneous flow of cement. A method of reducing the localized fractures due to the heterogeneous flow of bone cement at the tissue-cement interface by a functional nanofiber coating on cement has been developed in the present invention.

Figure 2:
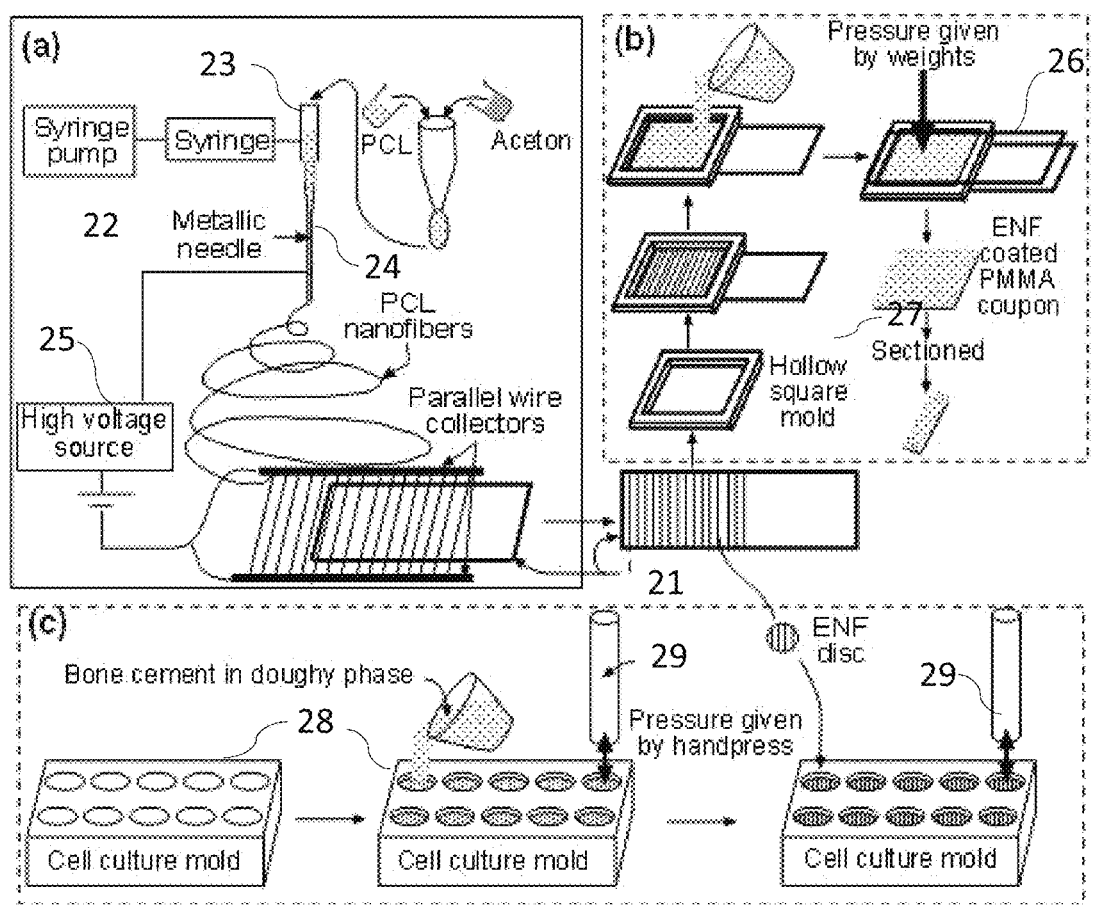
FIG. 2 is a non-limiting diagram showing schematic representation of major steps in the production methods for the present invention: step (a) single layer aligned PCL ENF membrane production, step (b) preparation of fiber coated cement test samples for surface and mechanical characterization, and step (c) preparation of fiber coated cement test samples for cytocompatibility test samples.

Referring to FIG. 2, a non-limiting diagram shows major steps in a novel process for fabrication of ENF fiber coating PMMA samples of biomechanical characterization: step (a) single layer aligned PCL ENF membrane production, step (b) preparation of fiber coated cement test samples for surface and mechanical characterization, and step (c) preparation of fiber coated cement samples for cytocompatibility test samples. This process was developed to produce test samples for experimental use in our clinical research directed to improving implant strength and stability. The process at (a) shows fabrication of ENF fiber coating PMMA samples of biomechanical characterization. A glass slide 21 (25×75×1 mm) was coated with aligned PCL nanofibers using an electrospinning setup 22. PCL pellets (7.69 wt %) were mixed with acetone in an ultrasonic mixer (Sonics & Materials, Inc., Newtown, Conn., USA). The sonication process was carried out at approximately 60° C. for 30 min. The solution was poured into a glass syringe 23 on an infusion pump (Harvard Apparatus, mode # PHD ULTRA) for the PCL fiber production. The PCL solution was ejected from the glass syringe 23 through an electrically-charged needle 24 (G blunt needle, 25 mm length, model # BX 25). The needle 24 was positively-charged by a high voltage (15 kV) DC power source 25 (Gamma High Voltage Research, Inc., model # ES 30 series) and two parallel wires were negatively-charged. The aligned PCL fibers were collected between the two parallel wires. To collect multiple layers of aligned fiber, the top surface of the glass slides 21 touched the aligned fiber stream, moved up, and then moved forward to repeat the process to collect twenty four layers of fibers (~1.6 micrograms) on the glass sides 21.

At process (b) in FIG. 2, a glass slide 26 without and with PCL ENF was secured on the bottom of a mold 27 using double-sided tape to prepare the control and ENF coated cement samples, respectively. According to the manufacturer recommendations, the PMMA solution was prepared by hand mixing 2.2 g of PMMA powder with 1.1 mL of methyl methacrylate (MMA) monomer using a powder: monomer ratio of 2:1. All solutions were cured in a custom-made aluminum mold 27 to prepare a solid block of PMMA sample of size 25×20×2 mm. Cement was poured into the chamber of the mold 27. Another glass side 26 was placed on top of the mold. Weights were stacked on the mold 27 to cure the cement under 60 kPa pressure (clinically applied pressure during orthopedic surgeries). The pressure was initiated at three minutes after the onset of mixing (although it may be possible to adjust the period) and was sustained throughout the curing period (approximately 15 min).

Referring again to FIG. 2 at process (b), to prepare blocks of control and ENF coated PMMA samples for the mechanical tests, a 20×25×2 mm control PMMA blocks was used. Mechanical test blocks were also used for the surface topographical analysis using confocal microscopy. Since both PCL ENF and PMMA cement have a white color, separate 20×25×2 mm ENF coated PMMA blocks were prepared for SEM imaging and mechanical tests. To prepare an ENF coated PMMA sample for SEM imaging, the PMMA solution was mixed with a red-colored dye before being poured into the mold. To prepare ASTM F417-78 standard flexural [29] test samples, (20×4×2) mm blocks were cut from the (20×25×2) mm block using a Buehler Isomet low-speed cutter. A (102×0.31×12.7) mm wafering blade was used for cutting the samples.

Referring to FIG. 2 at process (c), to prepare cytocompatibility of the control and ENF coated PMMA samples a custom made well 28 were prepared. PCL ENF were collected between the wires in process (a) until a fibrous cloth appeared. A 10 mm diameter PCL fiber disc was cut from the cloth using a punch (FIG. 12a). PMMA specimens were prepared by mixing 0.5 g of PMMA beads with 0.25 mL of MMA. All PMMA samples, while still pliable, were divided into 4 parts by a knife and were poured in the well. Each part of the samples was hand pressed during curing by a flat-ended 9.565 mm diameter highly polished round bar 29. The round bar 29 has clearance fits on the wells of the well plate. To prepare the ENF coated PMMA sample, a 10 mm diameter PCL fiber disc was placed on the cement and again pressed by the round bar 29 to attach the PCL fiber on the top of the PMMA. The sample wells were kept sterile in a biological safety cabinet under ultraviolet (UV) light for subsequent cell culture.

Figure 3:
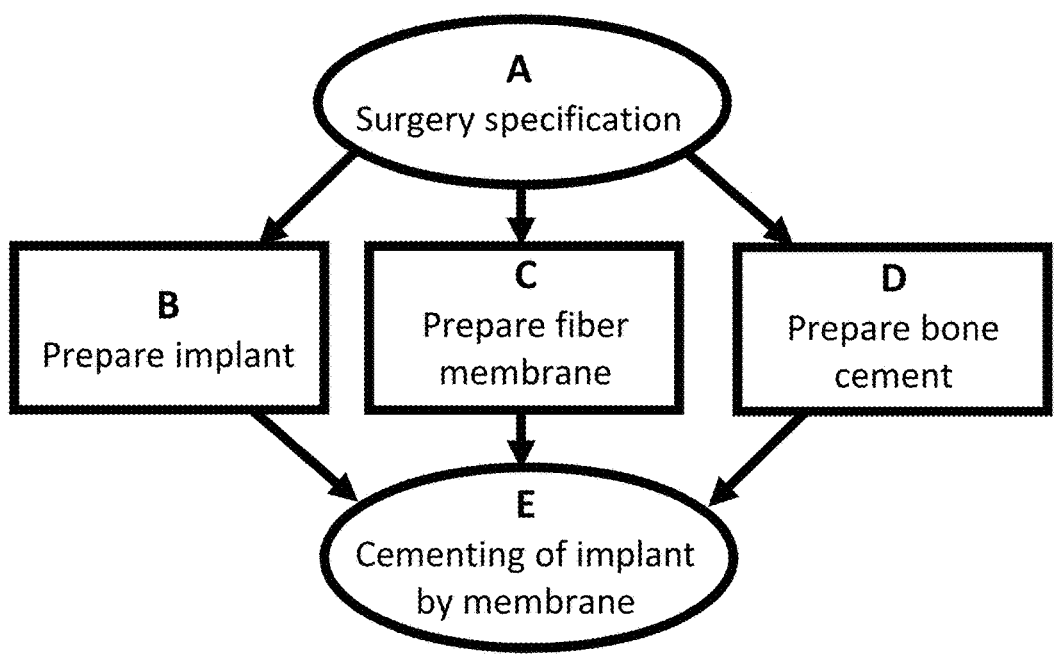
FIG. 3 is a non-limiting diagram showing a schematic view of the main steps required for the application of ENF membranes in a cemented implant surgery.

Referring now to FIG. 3, a non-limiting diagram of the method of the present invention is shown comprising five major steps: (A) Surgery specification; (B) Prepare Implant; (C) Prepare fiber membrane; (D) Prepare bone cement; and (E) Cementing of implant membrane.

Figure 4:
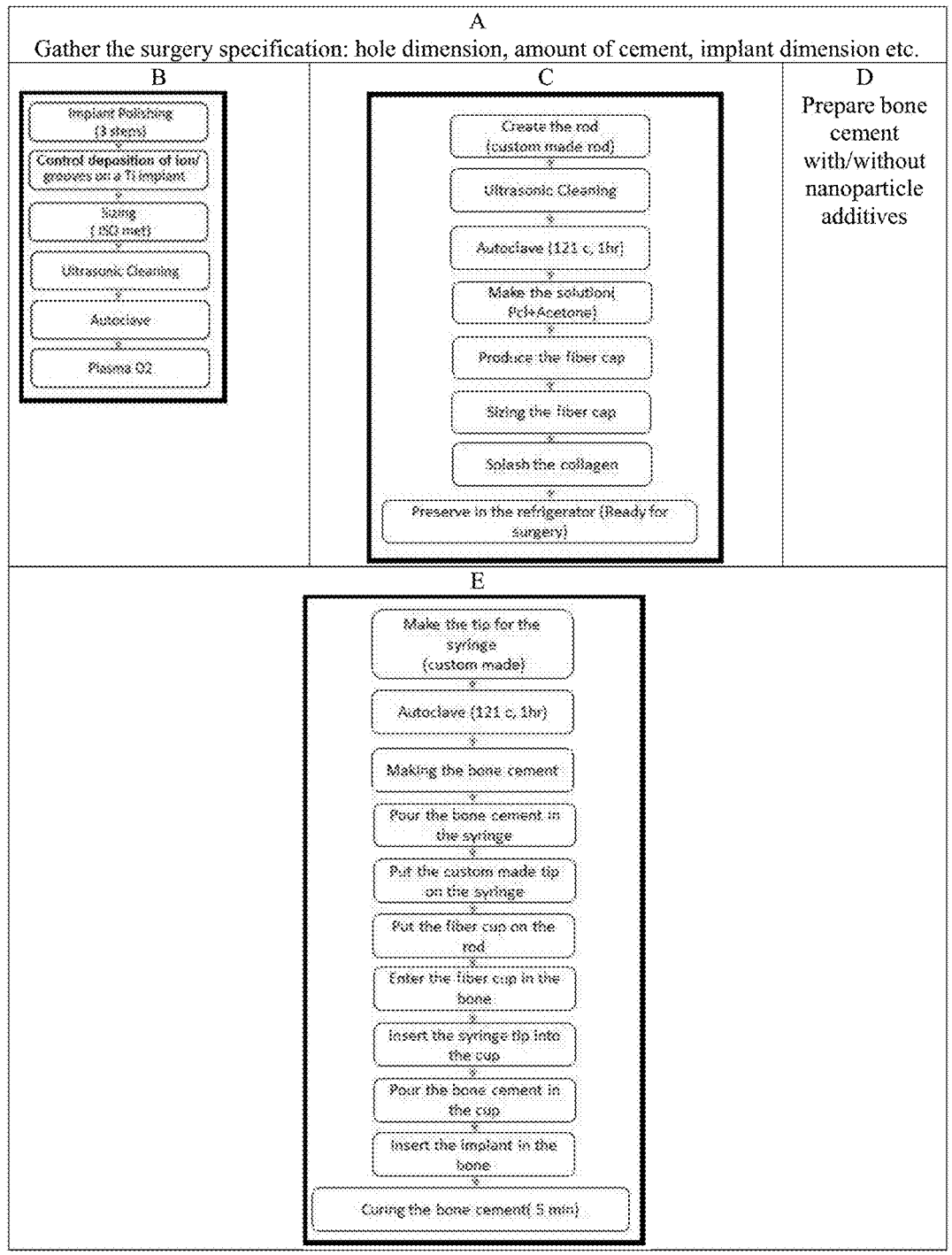
FIG. 4 is a non-limiting diagram showing a schematic view of the detail steps required for the application of ENF membranes in a cemented implant surgery.

Referring now to FIG. 4, the detail process in each step shown in FIG. 3 is illustrated. For a cemented implant surgery (ex. screw implant), the specification for surgery (e.g. hole dimension, implant size) must be known—step (A). The surgery specification determines the size and shape of ENF membrane that needs to be manufactured [see step (C)]. The present invention implements a set of grooves/ridges on a Ti implant—step (B) and fabricates a PCL ENF cylindrical membrane—step (C), that is placed in to the bio-surgery hole (formed cavity) for the cemented implant surgery. The grooves/ridges create mechanical interlock at the Ti/cement interface and PCL ENF cylindrical membrane creates osteoinductive and osteoinductive microenvironment at the bone/cement interface for the bone growth. Our experimentation demonstrated that mechanical stability of Ti/cement samples having microgrooves on Ti (5.14±0.68 MPa, n=6) that were created by machine sawing were significantly higher (15 times) compared to Ti/cement samples without microgrooves on Ti (0.34±0.14 MPa, n=6) due to the increase of Ti-cement contact area by microgrooving. Higher and more controlled Ti-bone contact area can be created by plasma nitrogen deposition on Ti at selective regions which will create TiN ridges or other ion deposition technique.

The ENFM cylindrical membrane (e.g., ENFM cup) was inserted into the hole (formed cavity). PMMA cement was prepared by hand mixing PMMA and MMA monomer with and without MgO nanoparticles using bead: monomer ratio of 2:1—step (D). Referring to step (E), the method of inserting the ENF cup into the hole (formed cavity) in the bone is indicated, where the ENFM cup is placed over a rod and inserted into the hole. Cement is injected into the ENFM cup, the implant is inserted and the cement is cured for approximately 5 minutes.

Figure 5:
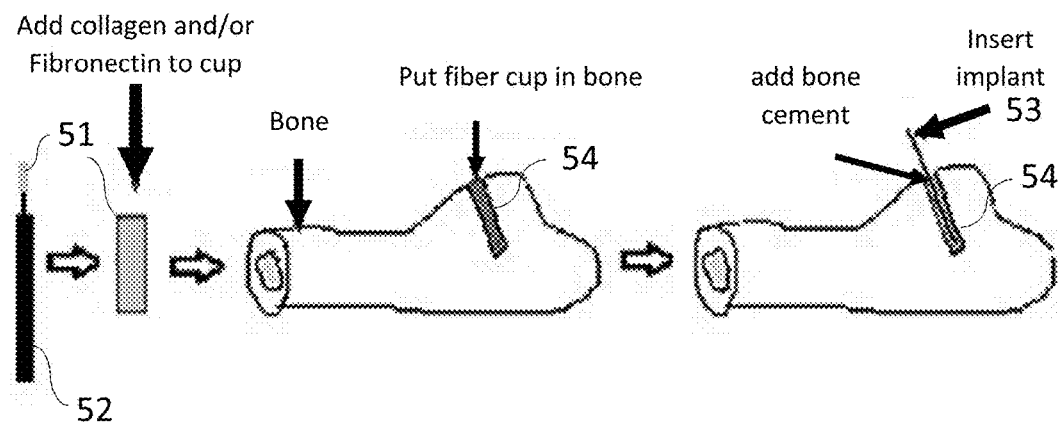
FIG. 5 is a non-limiting diagram showing a schematic view of the method of placing PCL ENF fiber cup in bone.

Referring to FIG. 5, the non-limiting diagram shows the process of the present invention where collagen and/or Fibronectin is added to the ENFM cup 51. The ENFM cup is placed into a hole (formed cavity) 54 using a rod 52 sized properly for that purpose. Bone cement is added by injecting it into the ENFM cup 51 using a syringe (see FIG. 10 C). The implant 53 is then inserted into the ENFM cup 51 positioned in the hole (formed cavity) 54 in the bone.

In our clinical studies, bilateral implantations were performed under anaesthetization on both legs of rabbits. A 2.96 mm diameter and 6 mm deep hole 54 was made by a hand drill in the rabbit femur. The PCL ENFM cup 51 was inserted into the hole 54 of a rabbit femur at the epiphyso-metaphyseal junction. The cement in the dough phase of mechanical properties during the polymerisation process was injected into the hole 54 of the ENFM cup 51 by a syringe (see FIG. 1 C). Subsequently, the implant 53 was hand-pressed into the cement.

Figure 6:
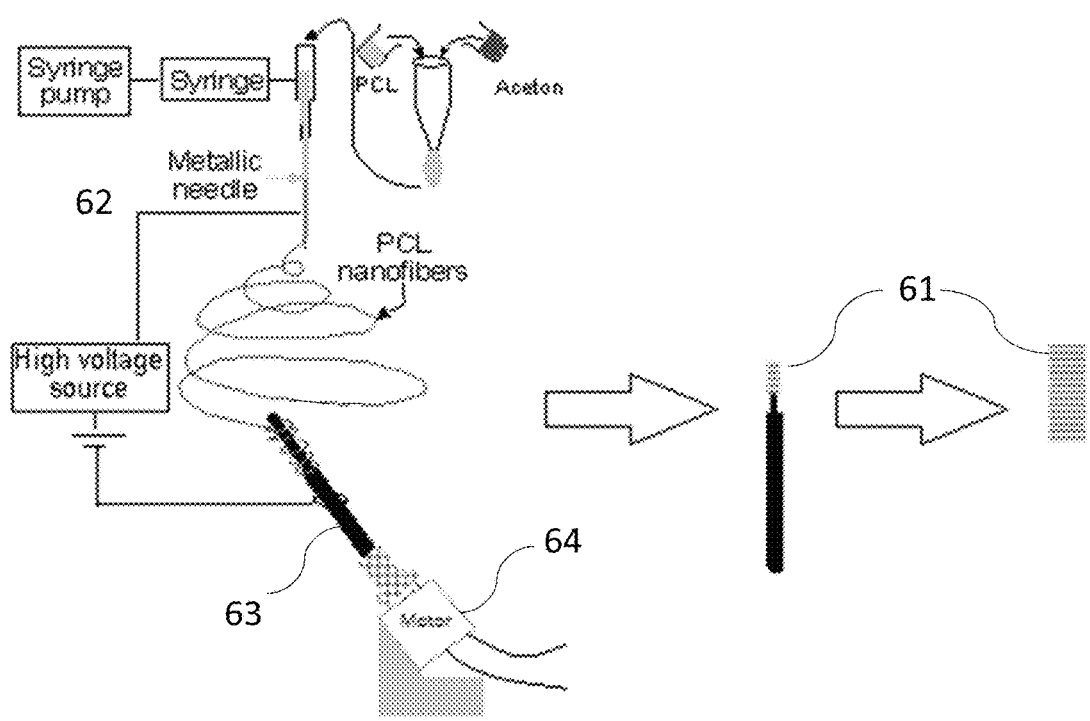
FIG. 6 is a non-limiting diagram showing a schematic view of the process for the production of PCL ENF fiber cup for the fiber coated cement surgery.

Referring now to FIG. 6, the schematic of the process for the production of PCL ENFM cup 61 is shown. Our developed electrospin unit 62 was used to create a cylindrical PCL ENFM cup 61 (length 7 mm, inside diameter 2.7 mm and thickness 0.1 mm) (FIG. 9 image C) by spraying PCL nanofibers on a rotating, round-shape collector 63 kept rotating by an electric motor 64. ENFM cup 61 provides a membrane that can act as resource for cell adhesion matrix protein (collagen, fibronectin) and antimicrobial agents (MgO, ZnO, Ag) to the adjoining bone tissue to have better osseointegration with the cement surface.

Figure 7:
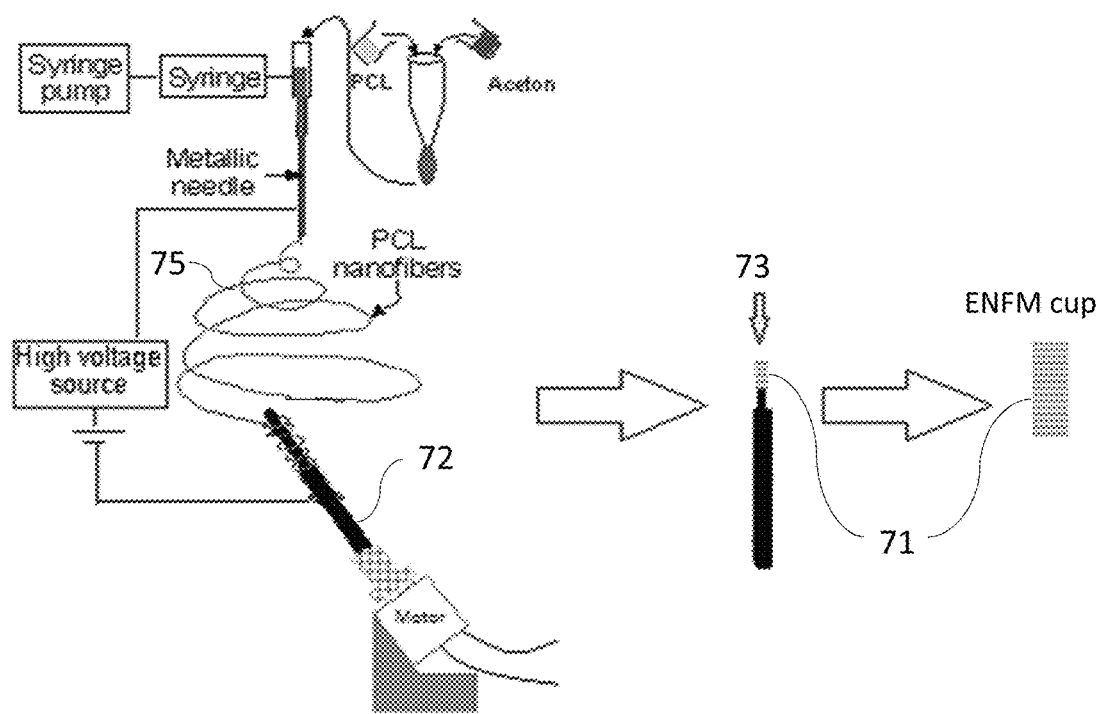
FIG. 7 is a non-limiting diagram showing a schematic view of the process for the production of PCL ENF fiber membrane with collagen and/or fibronectin.

Referring to FIG. 7, a non-limiting diagram shows the process of the present invention for immobilization of cell adhesion matrix protein (collagen and/or fibronectin). A ENFM cup 71 sized to fit a specific hole (formed cavity) in bone is produced by electrospinning fibers 75 onto a rapidly spinning cylindrical rod 72 with sufficient layers to produce a stiffened cylinder as a formed ENFM cup 71. Collagen and/or fibronectin is added 73 to the ENFM 71 cup. FN is a multifunctional protein most abundantly found in the ECM under dynamic remodeling conditions such as bone healing and development. FN has a large binding domain for attaching growth factor proteins such as rhBMP, TGF-β. FN reinforces perimatrix formation, where it serves as a biological glue mediating interaction between cells and ECM proteins. FN can be immobilized on Ti by tresyl chloride-activation process. FN contains a CG binding domain, so it can be polymerized into CG-PCL NFM.

In our clinical studies, cell viability tests were conducted on CG-PCL NFM coated samples with and without the plasma FN coating on Ti. Results showed reduced amount of cell attachment (p>0.05), but significant improvement of cell proliferation in NFM due to FN coating on Ti (p<0.05) suggesting that FN coating on Ti can further improve the biological functions of our NFM. Cellular FN can be used instead of plasma FN to increase the cell attachment on Ti, since cellular FN has better functionality for the regulation of bone scaffolding protein and higher adhesiveness than plasma FN.

Figure 8:
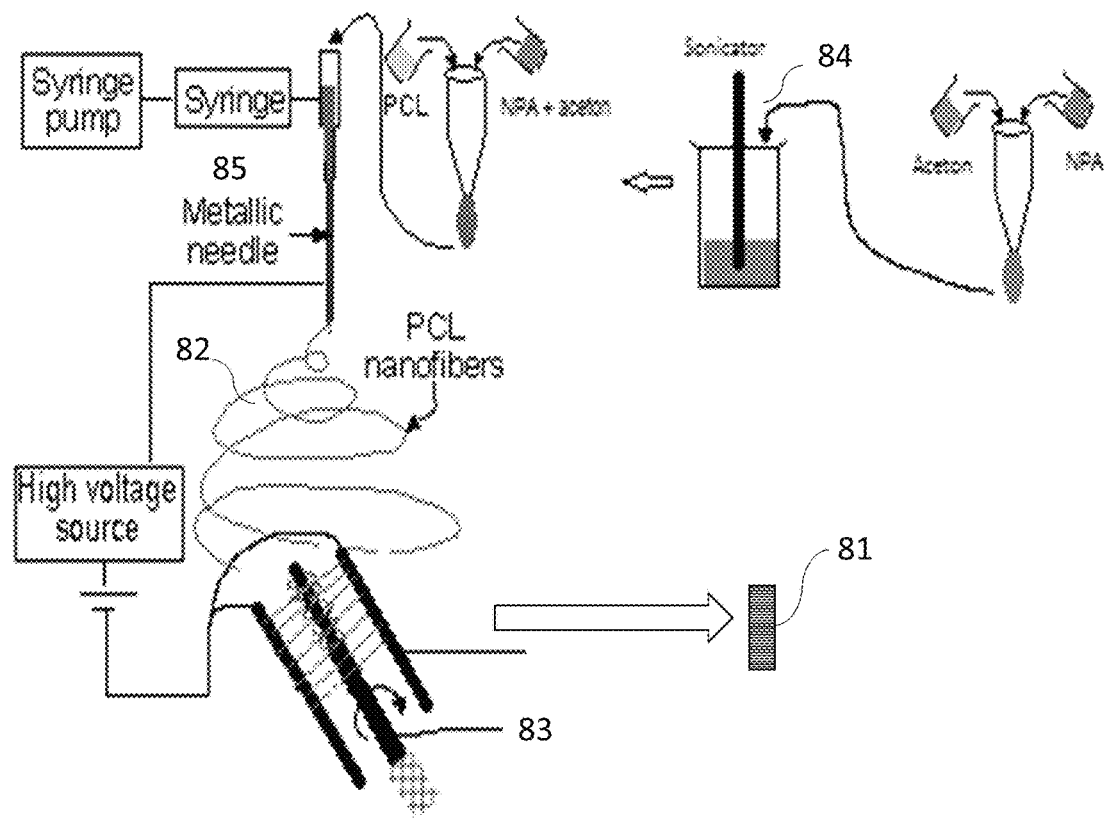
FIG. 8 is a non-limiting diagram showing a schematic view of the production of PCL ENF fiber cup with MgO nanoparticle tethered PCL.

Referring to FIG. 8, a non-limiting diagram illustrates the process of immobilization of nanoparticle additives (NPA) with PCL nanofiber. A preferred method is shown as a schematic of the process for production of PCL ENFM cup 81 using MgO nanoparticle tethered PCL. ENFM cup 81 is produced by electrospinning fibers 82 onto a rapidly spinning cylindrical rod 83 with sufficient layers to produce a stiffened cylinder. Using the methods of the present invention, we have tethered MgO NPs with PCL nanofiber. MgO NPs were sonicated 84 for a period of 30 minutes in acetone and then another 30 minutes with PCL beads to mix PCL with the solution. The MgO NP-PCL solution was used to produce nanofibers using an electrospun unit 85. In our research, we have used MgO, ZnO, Ag nanoparticle additives, which have osteoconductive and antimicrobial properties. The above nanomaterials are widely used to fabricate efficient gas sensors for the detection of various hazardous and toxic gases. For example, MgO is used for $SO_2$ gas sensors [Lee et al, Sensors and Actuators B: Chemical, vol. 160, pp. 1328-1334, Dec. 15, 2011], $TiO_2$ NP is used for low-temperature $CO_2$ gas sensors [Mardare et al, Ceramics International, vol. 42, pp. 7353-7359, May 1, 2016], ZnO NP is used for NO2 gas sensors [Kumar et al, Nano-Micro Letters, vol. 7, pp. 97-120, 2015//2015]. These NPAs can be tethered with the ultrafine fibers (see FIG. 15 images A, B, C) produced via electrospinning as a three-dimensional structured fibrous membrane with controllable pore structure and high specific surface area to produce membrane that can be used not only as a precision gas sensing device, but also as biomedical materials such as suture, skin grafting, protective coating on implant. The PCL nanofibers with NPA (MgO, TiO2, ZnO) were prepared by dissolving PCL and NPA (5% by wt of PCL) in 99.9% acetone (1000% by wt of PCL) and sonicating it for 30 min in 130 W and 20 kHz sonicator at 60% amplitude. Adding 5% of nano particles was discovered by trial and error method based on amount of MgO nano particles as it has the least density among the three.

Figure 9:
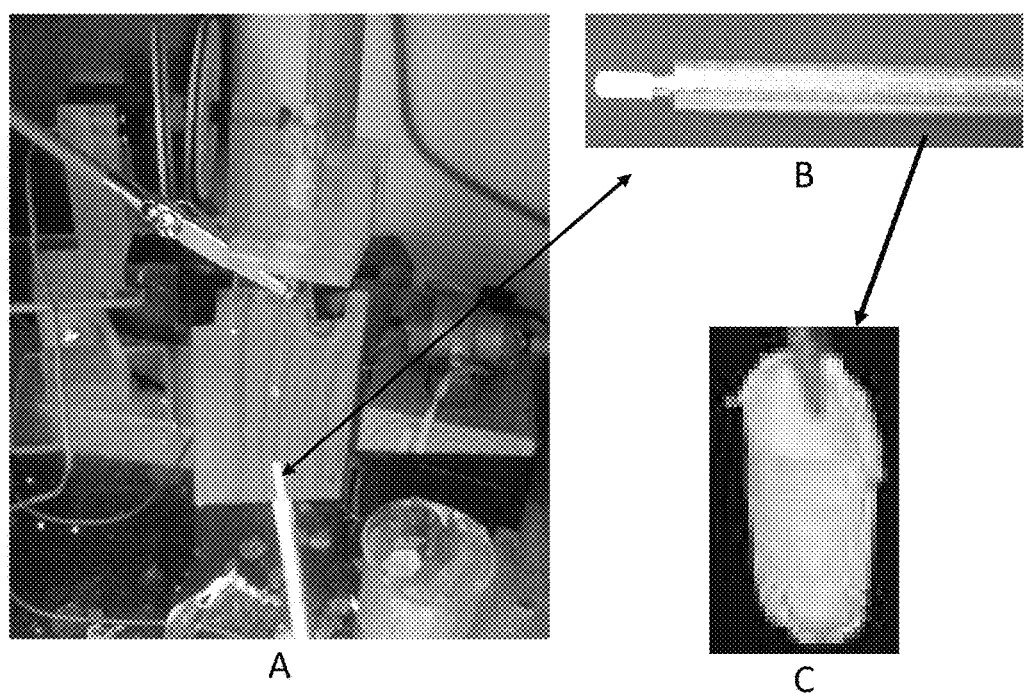
FIG. 9 is a captured image showing (A) the electrospin setup to produce PCL ENF membrane production, (B) membrane spun on to a custom made rod, and (C) the produced cylindrical cup shape membrane extracted from the perimeter of the rod.

Referring now to FIG. 9, a photograph of a PCL ENFM cup (image C) produced using the methods of the present invention is presented. Image A shows the electrospinning setup, and image B shows the metal rod on to which PCL nanofibers were collected to form the ENFM cup shown in image C. The exemplary fabricated cup shown has a length of 7 mm, inside diameter of 2.6 mm and PCL ENF membrane thickness of 0.2 mm. The size of the cup produced corresponds to the dimensions of the hole (formed cavity) created in bone to receive a specific implant.

Figure 10:
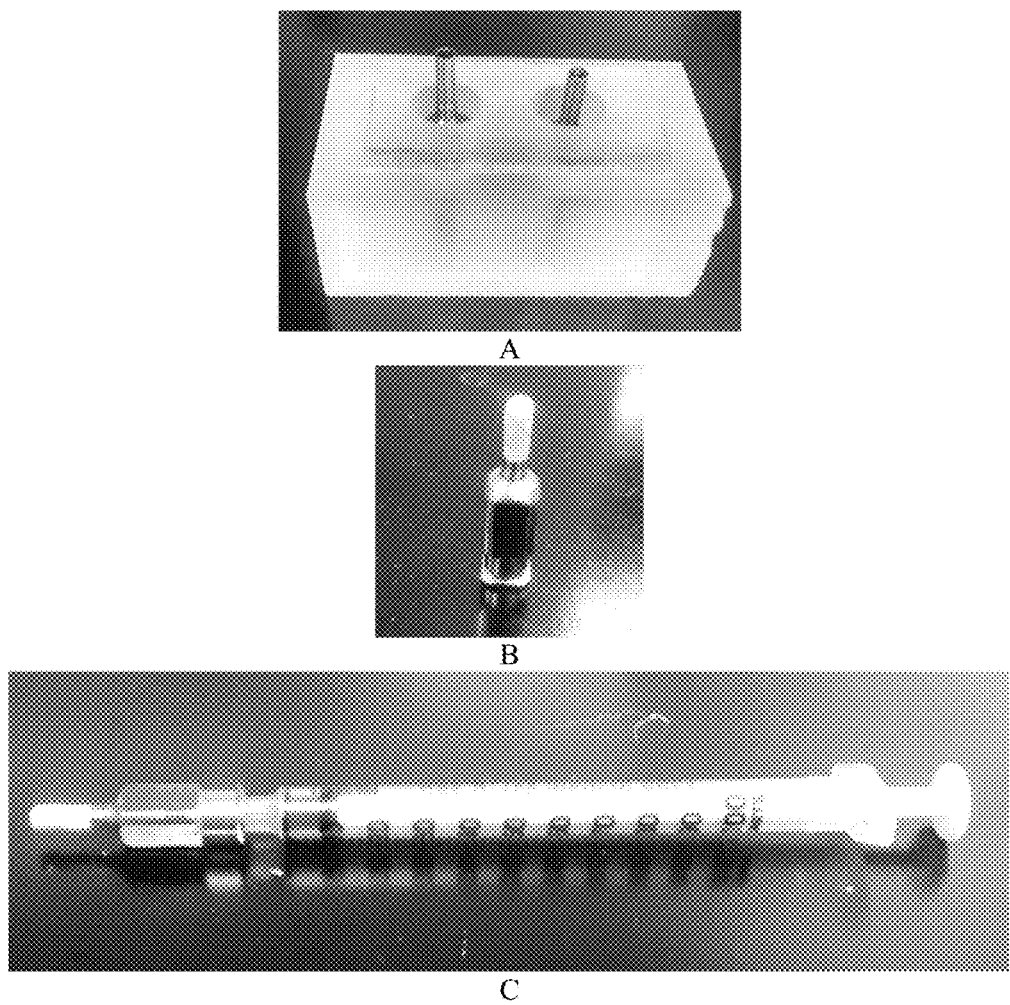
FIG. 10 is a captured image showing (A) the holder used for the carrier of fiber cup during animal surgery, (B) the cylindrical shape needle used inject cement after placing the fiber cup in the hole created for cementing an implant, (C) syringe used to push the cement in to the cup inside the surgery hole.

Referring now to FIG. 10, image (A) shows a custom made holder fabricated for our clinical studies and used to carry the ENFM cup under sterilize condition. A sterile tweezer was used to deliver the ENFM cup containing a needle [see image (B)] to a veterinarian for implantation of an implant by manually created defect site in rabbit femur. A 10 ml syringe shown in image C was loaded with bone cement. The needle with ENFM cup was secured with syringe. A 2.96 mm diameter and 6 mm deep hole was made by a hand drill in rabbit femur. The ENFM cup was inserted into the hole. PMMA cement was poured on the hole of the cup. Subsequently, the Ti wire was hand pressed into the cement.

Figure 11:
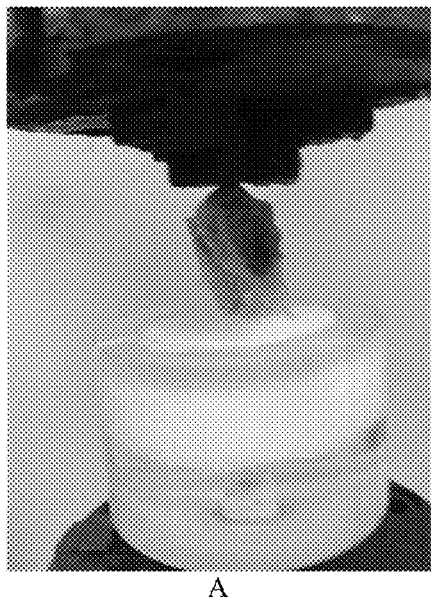
FIG. 11 is a captured image showing the fixation of a in vivo sample in a mechanical tester for the pull out tension test: (A) potting of the titanium anchored by PMMA bone cement sample in the mechanical test holder and (B) an implanted titanium anchored by PMMA bone cement using PCL ENF fiber cup after the mechanical test.
Figure 11:

Referring now to FIG. 11, an implanted titanium rod anchored by PMMA bone cement using PCL ENFM cup is shown before (image A) and after a mechanical test (image B). It is clear from image B that our invented PCL ENFM cup works for in vivo animal study and the cements were contained by PCL ENFM cup.

Figure 12:
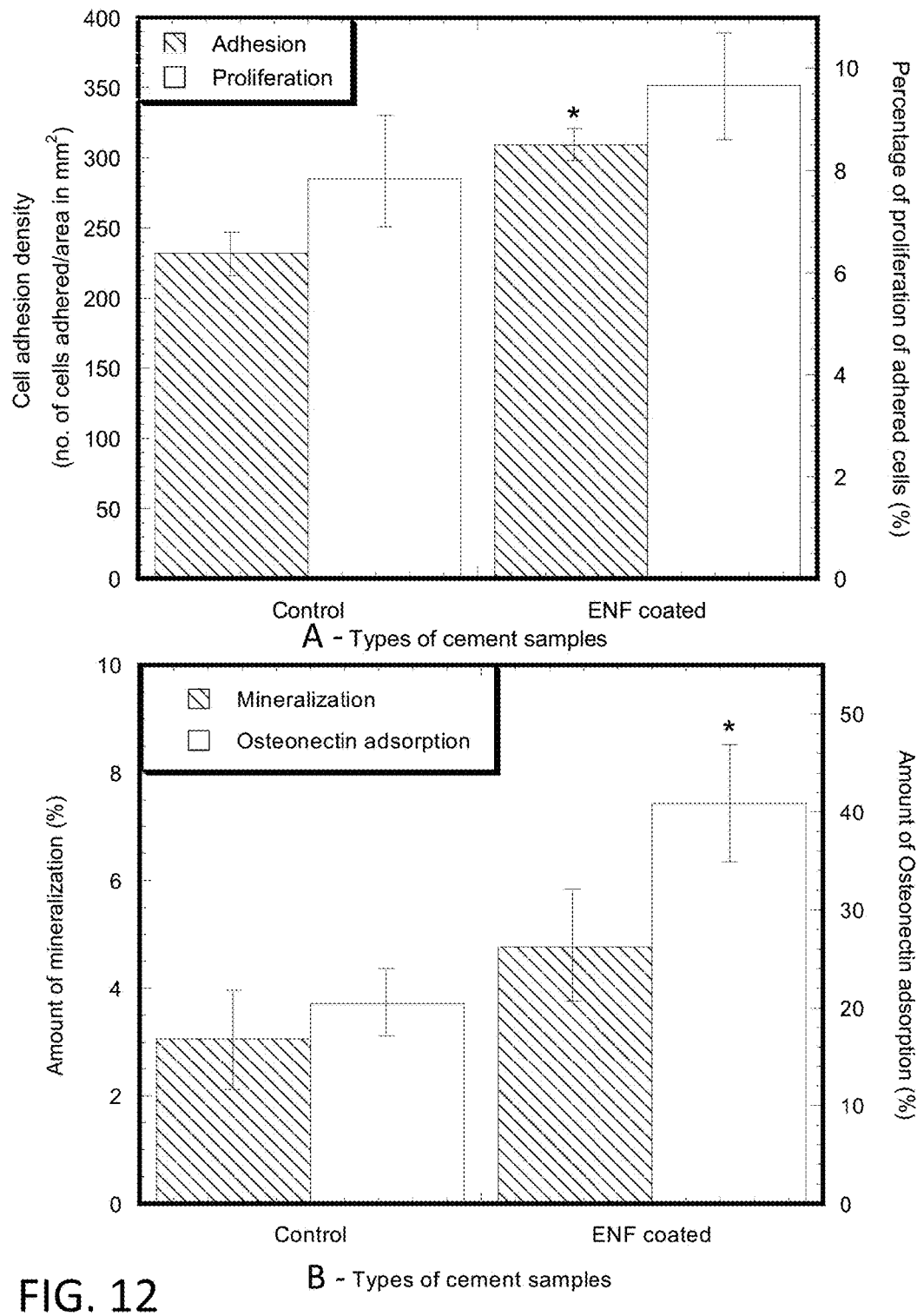
FIG. 12 is a non-limiting diagram showing the results of in vitro cell viability experiments on control and PCL ENF coated PMMA samples. (A) Mean cell adhesion density (±standard error) and the percentage of cell proliferation (±standard error) for the control and ENF coated PMMA groups after 48 h of cell culture. Data are presented with n=14 for both samples. (B) Mean amount of mineralization (±standard error) and mean amount of osteonectin (±standard error) for the control and ENF coated PMMA groups. Note: * p<0.05 (compared to control).

Referring to FIG. 12, graph A compares adhesion proliferation for the types of cement samples used in testing. Graph B shows mineralization and osteonectin adsorption for the types of cement samples used in testing. We have observed increased cytocompatibility properties (adhesion, proliferation, and protein adsorption) of the ENF coated PMMA implants compared to PMMA. This is because higher cell functions were created via better cell signaling arising from the cell-cell contact and the cell-ENF components in the ENF coated PMMA samples. Cell signals depend upon the physical (micro- or nano-structured surface topography, composition of ENF) and chemical properties of ENF. There exists differences of the physio-chemical properties between the control and ENF coated PMMA samples. The PCL nanofibers on PMMA lead to different physical characteristics viz. porosity and density due to the distribution of the PCL fiber. PCL in the ENF coated PMMA created a larger surface area that provided more cell binding sites. Additionally, PCL ENF can absorb numerous proteins or minerals akin to a cell membrane receptor, thus favoring cytocompatibility properties for the ENF coated PMMA samples compared to the control.

Figure 13:
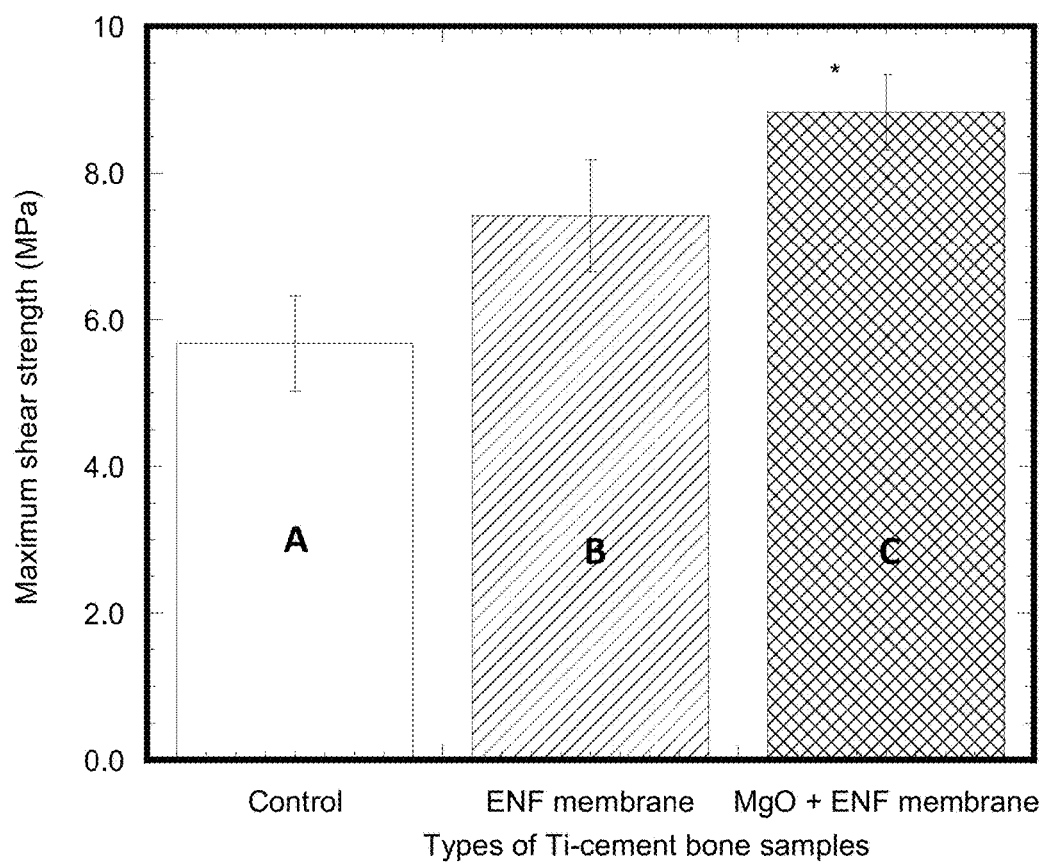
FIG. 13 is a non-limiting diagram showing results of pull out tension test on three group of samples: (A) control, (B) ENF membrane, and (C) MgO NPA incorporated Ti/cement samples.

Referring now to FIG. 13, in our clinical studies, three kinds of Ti/cement samples were prepared (A, B, C). They are Ti-PMMA (referred as control—A), with ENFM cup Ti-PMMA cement (referred as ENF membrane—B), with (C) Ti-PMMA cement where cement is anchored to bone via PCL ENF and MgO nanoparticles mixed with PMMA cement (referred as MgO +ENF membrane—C). For MgO +ENF membrane Ti/cement samples, PMMA cement was prepared by mixing 10 wt % of MgO nanoparticles with PMMA cement. Mechanical and CT scan images were conducted on the samples using an established method. We have found that both PCL ENFM cup with and without MgO incorporated cement significantly improves the mechanical stability of Ti/cement-bone joints. The ENF membrane acts as resource for bone growth molecules and antimicrobial agents to the adjoining bone tissue to have better osseointegration with the cement surface.

Figure 14:
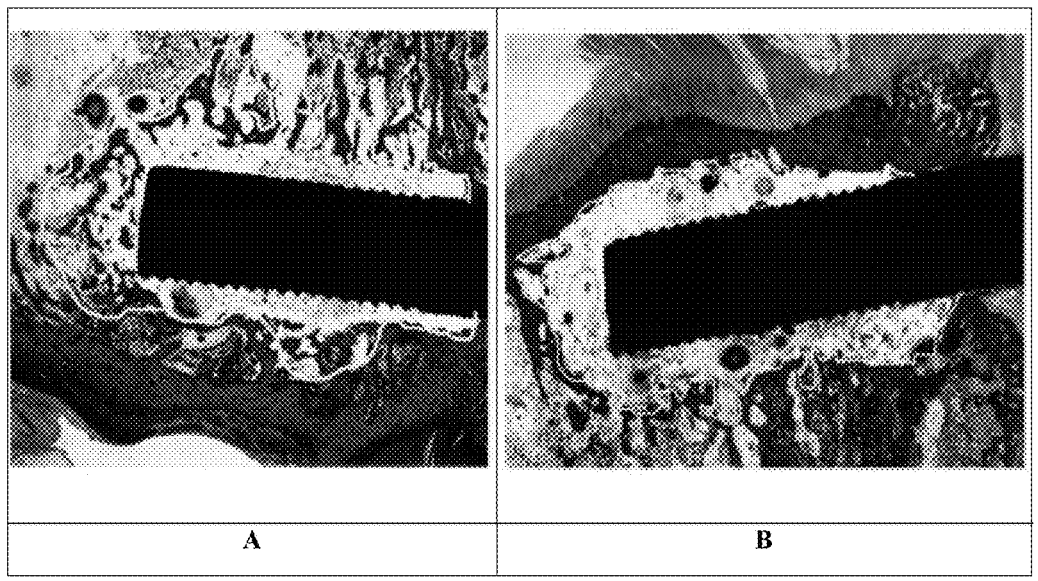
FIG. 14 is a non-limiting image showing results of histological experiments. (A) Control Ti-cement samples, and (B) ENF membrane covered Ti-cement samples

Referring to FIG. 14, a non-limiting image is presented showing results of histological experiments. (A) Control Ti-cement samples, and (B) ENF membrane covered Ti-cement samples. The present invention has proven through experimentation to be successful in increasing the in vivo mechanical stability (see FIG. 13) and no adverse effect on in vivo osseointegration as shown in the images of FIG. 14. Better MgO nanoparticles on in vivo mechanical stability is made possible by tethering MgO nanoparticles with PCL fiber using the methods of the present invention. All these observations and prediction are new and not reported in published literature or related art.

Figure 15:
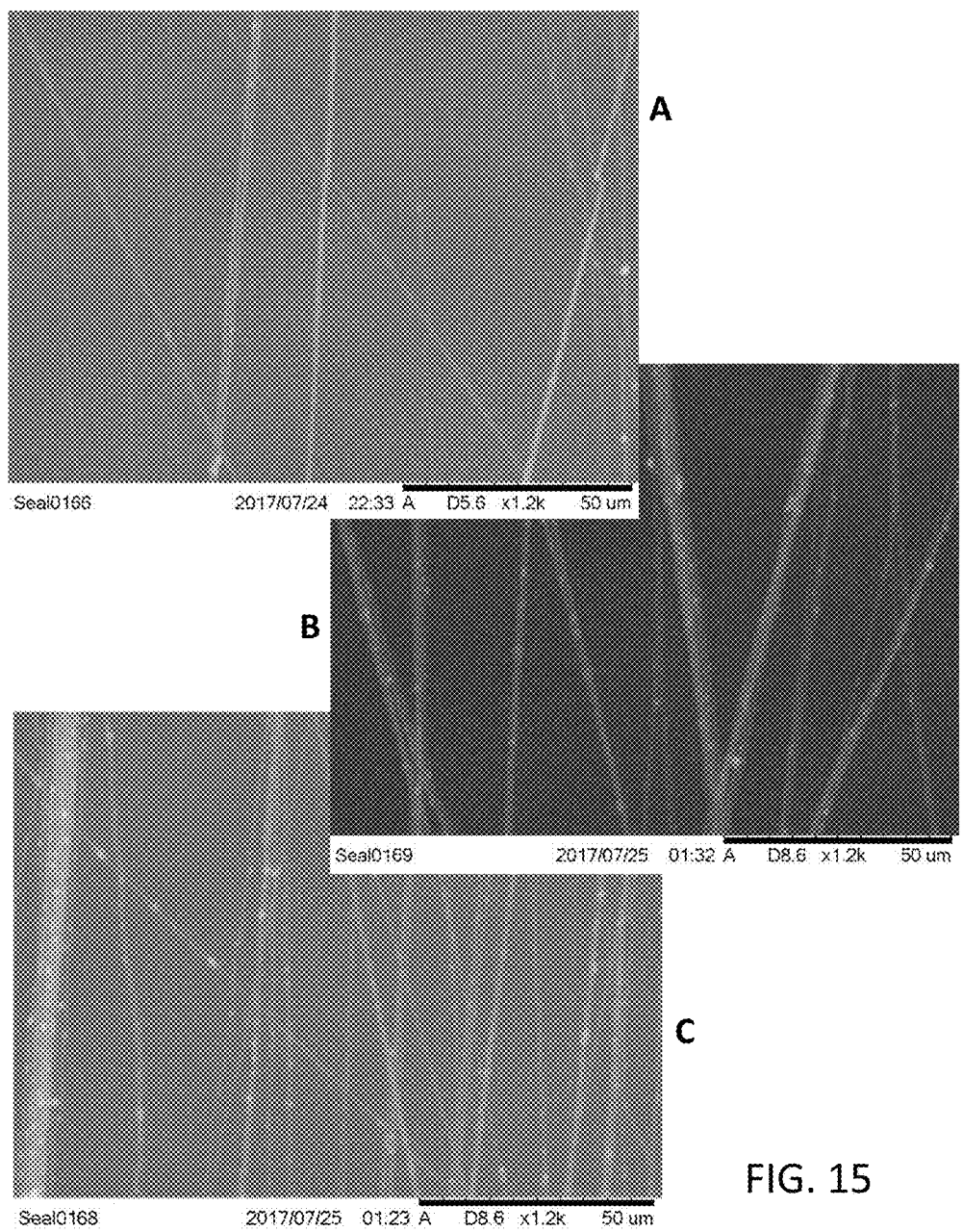
FIG. 15 is a non-limiting diagram showing results of the tethering of 5 wt % (A) MgO, (B) ZnO and (C) $TiO_2$ immobilized PCL ENF.

Referring to FIG. 15, nanoparticle drugs (osteoconductive and antibacterial) are shown (white dots) tethered with nanofiber. Using the methods of the present invention (FIG. 8), we have successfully tethered MgO, ZnO and $TiO_2$ NPs with PCL nanofiber. The MgO NP-PCL, MgO NP-PCL and TiO2 NP-PCL solutions were used to produce MgO, ZnO and TiO2 tethered PCL nanofibers using an electrospun unit. The attachment of the nano particles was confirmed by taking SEM images of the samples (FIG. 15 images A, B, C). The sample was kept under the running water flow for a minute and images were taken again to confirm the nano particle's attachment. It has been observed from animal studies that coating of microgrooves on titanium with collagen (CG)-poly(ε-caprolactone) (PCL) nanofiber mesh (NFM) improves the mechanical stability and osseointegration of titanium (Ti). Moreover, histomorphometric analysis showed that bone ingrowth to Ti surface increased by coating microgrooves with the CG-PCL NFM. Further, NFM can be a carrier of nanoparticle minerals at the implant sites that can influence the mechanical stability and osseointegration of Ti with bone. We have investigated whether mixing of MgO nanoparticle with CG-PCL NFM has any influence on the mechanical stability and osseointegration of Ti. We have measured the effect of MgO nanoparticles on the in vitro cytocompatibility properties (osteoblast cell adhesion, proliferation, differentiation and protein adsorption) of CG-PCL NFM coated Ti. We have also measured the effect of MgO nanoparticles on the in vivo mechanical stability and osseointegration of CG-PCL NFM coated Ti with bone. Our research found that cell adhesion/proliferation, and mineralization/protein adsorption of MgO NP added CG-PCL NFM coated Ti was significantly higher compared to CG-PCL NFM ($p<0.05$). Both CG-PCL and CG-MgO-PCL treatment on Ti significantly influenced the in vivo mechanical stability of the Ti as compared to groove only samples, but there is no significance difference of mechanical stability found between CG-PCL and CG-MgO-PCL treated samples. Mechanical results showed that shear strength of Ti with bone for MgO added CG-PCL NFM coated ($5.97\pm0.65$ MPa, n=6) was higher compare to fracture strength of Ti CG-PCL NFM ($4.79\pm0.39$ MPa, n=6) ($p>0.05$). Local delivery of protein and mineral to titanium is possible using the methods of the present invention via CG-PCL electronspun nanofiber matrix coating for cementless implant surgery. Similarly, local delivery of protein and mineral to cement with ENF fiber coating is possible using the methods of the present invention to tether nanofibers with MgO, ZnO and $TiO_2$ biomolecules (FIG. 15). Tethering nanofibers with MgO, ZnO and $TiO_2$ biomolecules creates a better osteoconductive and antimicrobial platform at the cement/bone interface that reduces implant loosening by increasing osseointegration and decreasing infection. The biological properties of a functional coating can be further improved by adding growth factors, genes, and other biomolecules (such as hydroxpapatite, bisphosphonate) to create a truly osteoinductive platform at the cement/bone interface. Currently, no published research has been found reporting adding the above factors to PCL ENF. Without the addition of bone growth molecules, the invention shows significant improvement of mechanical stability. Even further enhancement of mechanical stability and osseointegration is achieved by adding bone growth molecules or proteins with the PCL ENF in accordance with the methods of the present invention.

Figure 16:
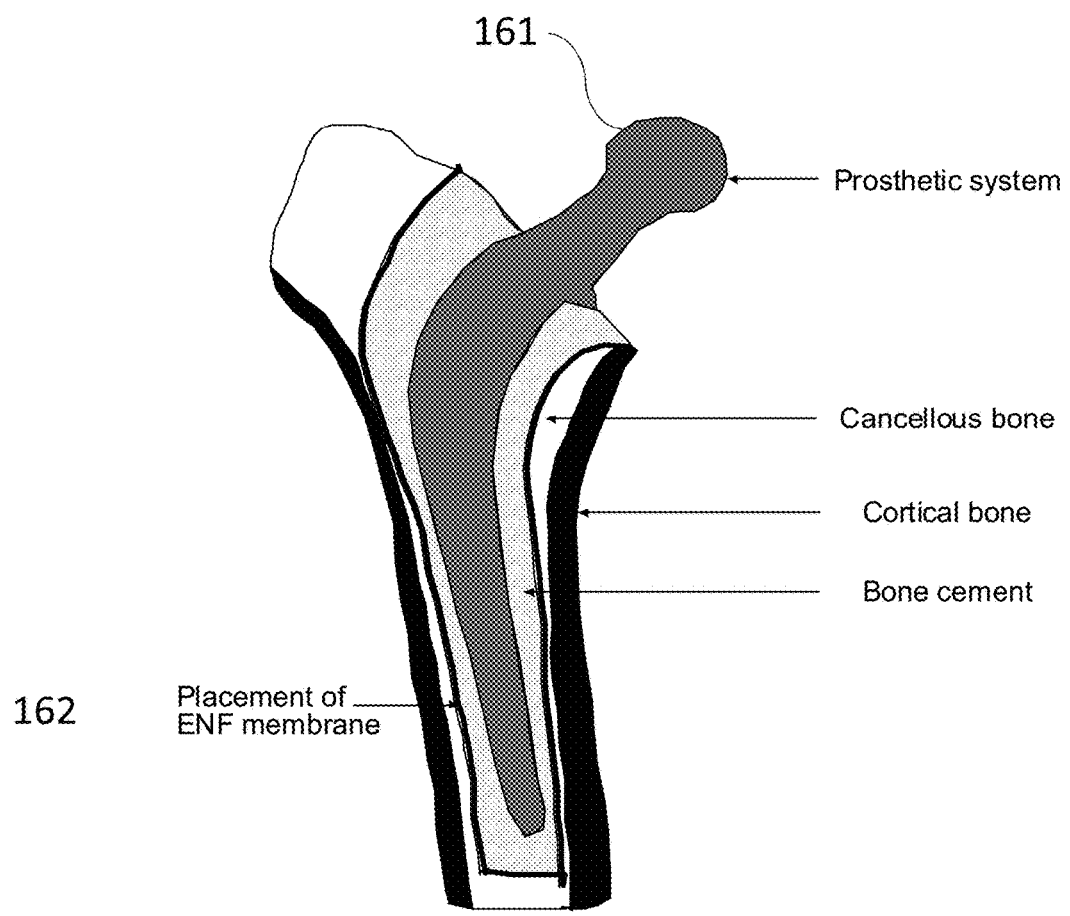
FIG. 16 is a non-limiting diagram showing results of the application of the innovation on the cemented hip surgery

Referring to FIG. 16, the method provided by the present invention can be used to apply ENF membrane to a cemented hip implant 161, where the shape and size of the ENF membrane 162 can be the same as the shape and size of the hole drilled for the anchor of the cemented hip implant 161. A custom made aluminum block can be machined to the shape of the hole. ENF fibers can be deposited on the custom made block. The membrane can be placed as marked in FIG. 16 and subsequently cement and implant can be pressed in to the hole (formed cavity).

Our experimentation revealed that the in vitro biocompatibility of cement is improved by addition of PCL ENF membrane with PMMA (FIG. 12). Experimentation revealed that the in vivo mechanical stability of bone/PMMA interface is improved by addition of PCL ENF membrane cup and magnesium oxide (MgO) nanoparticles with PMMA (FIG. 13). Potential applications in surgery for the methods provided by the present invention include osteoporotic bone where cement is used to hold the implant, but due to the void space of the bone and to osteoporotic disease, cement penetrates some of narrow channeled void space. When cemented, such void space has higher probability of fracture by applied physiological loading. By using the PCL ENFM cup produced by the methods of the present invention, filling the narrow void space by ENF membrane with local drug, such failure of cement at the bone-cement interface can be avoided. In addition, the PCL ENF fiber material can serve as reservoir by tethering nanoparticles (FIG. 15) for the local delivery of nanomedicine for the orthopedic bone disease.

The controlled fabrication of microgrooves on Ti surfaces by plasma nitriding is significant, since such grooving can be applied to complex shape implant surfaces such as hip and dental implants, which is impossible by machine sawing. Our invented NFM coating can serve as a reservoir for controlled release of antimicrobial and growth factor molecules for reducing infection and promoting osteogenesis at the cement/bone interface. Providing osteogenesis pathways and the enhanced activities induced by NFMs will greatly facilitate bone repair.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. An electrospun nanofiber (ENF) membrane, comprising:
   a fiber matrix exhibiting a tubular shape having an inside span and an outside span, said matrix formed by electrospinning nanofibers on to an elongated substrate rotated around a longitudinal axis during electrospinning to produce said tubular shape;
   multiple layers of nanofibers, each of said layers consisting of generally aligned fiber strands and said fiber strands comprising each layer are collectively positioned at an oblique angle to the fiber strands in each adjacent layer to form said matrix, said matrix comprising no more than 24 layers of nanofibers; and
   nanoparticle additives (NPA) immobilized with poly-ε-caprolactone (PCL) nanofiber.

2. The electrospun nanofiber (ENF) membrane of claim 1, further comprising growth factors immobilized collagen-poly-ε-caprolactone nanofiber matrix (CG-PCL NFM).

3. The electrospun nanofiber (ENF) membrane of claim 1, further comprising fibronectin (FN) and magnesium oxide nanoparticles (MgO NPs) immobilized CG-PCL NFM.

4. The electrospun nanofiber (ENF) membrane of claim 3, wherein said FN is immobilized using a tresyl chloride-activation process.

5. The electrospun nanofiber (ENF) membrane of claim 1, further comprising immobilized cell adhesion matrix protein (collagen, fibronectin) and bone growth molecules (rhBMP, TGF-($\beta$)).

6. The electrospun nanofiber (ENF) membrane of claim 1, further comprising tethered antimicrobial and osteoinductive molecules (MgO, ZnO, Ag).

7. The electrospun nanofiber (ENF) membrane of claim 1, further comprising using MgO, ZnO and $TiO_2$ biomolecules with PCL ENF membrane to create a osteoinductive and antimicrobial platform.

8. The electrospun nanofiber (ENF) membrane of claim 1, wherein said membrane is constructed with at least one end layer of nanofibers to form a cup.

9. The electrospun nanofiber (ENF) membrane of claim 1, wherein said membrane is adapted to provide mechanical stability and osseointegration of PolyMethylMethAcrylate (PMMA) cement with bone in surgeries that use a metallic implant.

10. The electrospun nanofiber (ENF) membrane of claim 9, where porosity of said ENF membrane is sized to prevent penetration of said PMMA cement into void space within said bone tissue.

11. The electrospun nanofiber (ENF) membrane of claim 10, further comprising nanoparticle additives (NPA) MgO, ZnO, and Ag tethered with PCL in the ENF by dissolving PCL and NPA (4% to 6% and preferably 5% by weight of PCL) in acetone (900% to 1100% and preferably 1000% by weight of PCL), sonicating the mixture, and electrospinning the PCL with NPA.

12. The electrospun nanofiber (ENF) membrane of claim 11, where said membrane is formed as a cup using said ENF, and exhibits adequate stiffness and porosity to control movement of said cement into said bone.

13. The electrospun nanofiber (ENF) membrane of claim 12, wherein said nanofiber membrane is adapted to be inserted into a formed cavity in said bone, and receive said PMMA cement and said implant.

* * * * *